United States Patent
Morita et al.

(10) Patent No.: US 8,221,967 B2
(45) Date of Patent: Jul. 17, 2012

(54) METHOD FOR QUANTIFICATION OF PEPTIDE AND PROTEIN

(75) Inventors: Yoshikazu Morita, Kawagoe (JP); Aiko Ono, Kawagoe (JP); Atsushi Serizawa, Kawagoe (JP); Hiroshi Kawakami, Kawagoe (JP)

(73) Assignee: Megmilk Snow Brand Co., Ltd., Sapporo (JP)

(*) Notice: Subject to any disclaimer, the term of this patent is extended or adjusted under 35 U.S.C. 154(b) by 414 days.

(21) Appl. No.: 12/521,632

(22) PCT Filed: Dec. 27, 2007

(86) PCT No.: PCT/JP2007/075061
§ 371 (c)(1),
(2), (4) Date: Aug. 4, 2009

(87) PCT Pub. No.: WO2008/081849
PCT Pub. Date: Jul. 10, 2008

(65) Prior Publication Data
US 2011/0039287 A1 Feb. 17, 2011

(30) Foreign Application Priority Data
Dec. 28, 2006 (JP) ................. 2006-356161

(51) Int. Cl.
*C12Q 1/00* (2006.01)

(52) U.S. Cl. ........... 435/4; 435/7.4; 435/28; 313/564

(58) Field of Classification Search ........ 435/4
See application file for complete search history.

(56) References Cited

FOREIGN PATENT DOCUMENTS

| JP | 2006-105699 | 4/2006 |
|----|-------------|--------|
| JP | 2006-300752 | 11/2006 |
| JP | 2006-300758 | 11/2006 |
| WO | 2006/002841 | 1/2006 |

OTHER PUBLICATIONS

Zappacosta et al. "N-terminal isotope tagging strategy for quantitative proteomics: results-driven analysis of protein abundance changes", Anal. Chem. 2004, 76:6618-6627.*
Cohen A M et al.: "Absolute quantification of Atlantic salmon and rainbow trout vitellogenin by the 'signature peptide' approach using electrospray ionization QqToF tandem mass spectrometry" Journal of Mass Spectrometry John Wiley and Son Ltd, vol. 41, No. 5, May 5, 2006, pp. 646-658, XP002573021.
Carlsson K C et al.: "Sample preparation and determination of gabapentin in venous and capillary blood using liquid chromatography-tandem mass spectrometry." Journal of Pharmaceutical and Biomedical Analysis, vol. 34, No. 2, Feb. 4, 2004, pp. 415-423, XP002573022.
Thompson A et al.: "Tandem mass tags: A comparative analysis of complex protein mixtures by MS/MS" Analytical Chemistry 20030415 American Chemical Society US, vol. 75, No. 8, Apr. 15, 2003, pp. 1895-1904, XP002573023.
European Patent Office issued an European Search Report dated Mar. 26, 2010, Application No. 07860283.6.
International Search Report—PCT/JP2007/075061—Mar. 11, 2008.
Ken Iguchi et al., "Naibu Hyojun ni Antei Doitai o Mochiita Electrospray Ionization Shitsuryo Bunsekiho ni yoru HbA1cBunsekiho no Kakuritsu" , Bulletin of the Fujita Medical Society, vol. 28, No. 1, Oct. 28, 2004, pp. 45 to 48.

* cited by examiner

*Primary Examiner* — Susan Hanley
*Assistant Examiner* — Bin Shen
(74) *Attorney, Agent, or Firm* — Young & Thompson

(57) ABSTRACT

A determination method quantifies a specific protein or peptide contained in a trace amount with high accuracy and in a simple manner without the need of using any expensive reagent. A protein or peptide of interest can be quantified by LC/MS/MS by using, as an internal standard, a protein or peptide including an amino acid sequence having the reshuffling the binding order of amino acid residues in the amino acid sequence for the protein or peptide of interest.

13 Claims, 1 Drawing Sheet

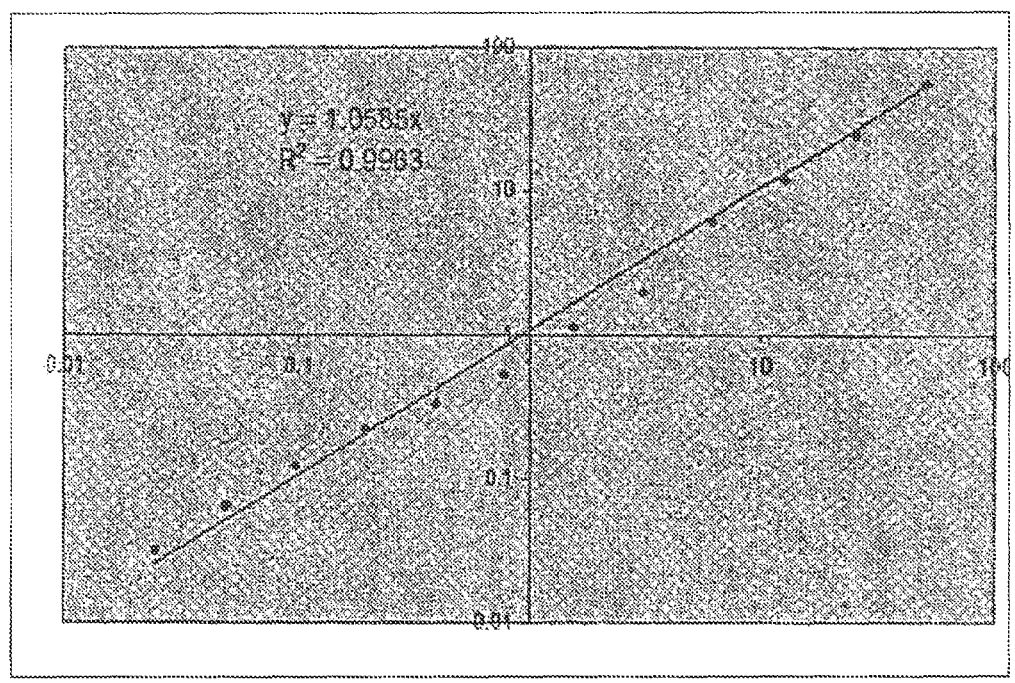

METHOD FOR QUANTIFICATION OF PEPTIDE AND PROTEIN

TECHNICAL FIELD

The present invention relates to a measurement method which can quantify a specific protein or peptide contained in a trace amount with high accuracy and ease, and even without using any expensive reagent.

BACKGROUND ART

ELISA using an antibody to a specific protein is known as a method of quantifying a specific protein contained in a trace amount in a measurement sample. However, in order to prepare the antibody, it is necessary to prepare a highly pure peptide or protein serving as an antigen, and to prepare an antiserum by administering the peptide or protein to an animal, and the procedure is thus very troublesome. In addition, an antibody may react with a highly homologous protein, and hence it is necessary to examine whether only a specific protein is measured.

In addition, reactivity of a protein with an antibody varies due to thermal denaturation and the like. Therefore, in a sterilized product, such as food, it is impossible to determine the protein content with high accuracy even if a specific protein is measured by ELISA described above.

Quantitative analysis methods for proteins, which have developed rapidly in recent years, include a method using a high performance liquid chromatogram tandem mass spectrometer (hereinafter, referred to as LC/MS/MS). A method has been developed for identifying a protein, which involves performing separation of a sample containing many kinds of proteins by two-dimensional electrophoresis and measuring peptides by LC/MS/MS obtained by an enzymatic treatment of the resultant spots. If measurement is performed by LC/MS/MS, There are the following advantages: it is possible to reduce the steps of pretreatment because derivatization is unnecessary, which is required in conventional GC/MS; and it is possible to measure a polymer compound such as a protein or peptide. In a method of identifying a protein by LC/MS/MS, the protein becomes able to be identified by: determining the mass of a peptide fragment produced from a sample protein using a specific protease by the first MS; fragmenting the peptide; performing the second MS to anticipate the amino acid sequence of the peptide; and comparing all the anticipated peptide sequences with a database.

As the method of quantifying a protein by LC/MS/MS, a method which involves labeling an amino acid in a target peptide with deuterium and measuring the amino acid has been reported (see Non-Patent Document 1, for example). However, in this method, the deuterium-labeled amino acid is used as internal standard substances, and because the deuterium-labeled amino acid is very expensive and rare, the peptide synthesis using the method may limit the application thereof.

In addition, a method of detecting an animal-derived protein in a complex mixture by LC/MS/MS is disclosed (see Patent Document 1, for example). However, this method has a difficulty in removing interfering substances and maintaining the level of contaminants at a low level and also requires cumbersome procedures.

There is required a measurement method which can quantify a specific protein or peptide contained in a trace amount with high accuracy and ease, and even without using any expensive reagent.

[Patent Document 1] JP 2005-513481 B
[Non-Patent Document 1] David R. Barnidge et al., Analytical Chemistry, Vol. 75, No. 3, 2003

SUMMARY OF THE INVENTION

An object of the present invention is to provide a measurement method which can quantify a protein or peptide with ease and higher accuracy and without using any expensive reagent.

The inventors of the present invention have searched for a measurement method which can quantify a protein or peptide with higher accuracy. As a result, the inventors have found the following method. In the case of measurement of a protein A, first, the protein A is decomposed with an enzyme to produce a peptide B. A part of the amino acid sequence of the peptide B is replaced to produce a peptide C, and measurement by LC/MS/MS is performed using the peptide C as an internal standard. Meanwhile, in the case where the protein A is separated from a measurement sample and then decomposed with an enzyme, in order to correct the recovery rate in the separation operation, a protein having properties similar to the protein A is required as an internal standard for the protein A. Therefore, a protein D which is more similar to the protein A but is not the protein A may be obtained by replacing the sequence of the peptide B in the protein A by the sequence of the peptide C. The inventors have found out that the peptide B can be measured in the same manner as in the case of using the peptide C by using the protein D as an internal standard.

As described above, the inventors of the present invention have found that a protein or peptide to be measured can be quantified by LC/MS/MS using, as an internal standard, a peptide obtained by changing a part of the binding order of amino acids in an amino acid sequence of a specific peptide in a protein to be measured without changing most of the properties of the original peptide, and this finding has thus led to the completion of the present invention.

By changing the binding order of amino acids in the amino acid sequence in a specific peptide of a protein to be measured, the specific peptide in the protein to be measured and the internal standard peptide behave as substances having the same molecular weight in the first MS, and the two peptides can be separated based on the difference in the amino acid sequences in the second MS. Based on the ratio of the signal intensities of respective peptides determined by the second MS, the concentration of the protein to be measured can be quantified. The measurement method of the present invention may improve the measuring accuracy in comparison with a single-step MS because selection based on the mass is performed in two steps. Moreover, the method can confirm that only a specific protein is measured because information on the amino acid sequence can be obtained at any time by the second MS. Meanwhile, a conventional method where a peptide including a deuterium-labeled amino acid is used as an internal standard, is performed while switching the measurement of a target peptide and measurement of the internal standard peptide in the first MS, resulting in lowering of the accuracy in the measurement. On the other hand, the method of the present invention can be performed with high accuracy because the molecular weight of the target peptide is the same as that of the internal standard peptide. As described above, the method of the present invention can be conducted only by changing the binding order of amino acids in an amino acid sequence, and thus the analysis method is easy. In addition, measurement can be performed without using any expensive reagent. Moreover, the internal standard peptide may be prepared using an existing peptide synthesizer, and thus the method of the present invention has an advantage over the conventional measurement method in terms of cost.

A protein obtained by replacing the amino acid sequence is very easily prepared by replacing the sequence on a genetic level according to the development of genetic technology. If the protein having a change in the binding order of amino acids in the amino acid sequence can be used as an internal standard, a measurement with higher accuracy can be achieved because the protein behaves as an internal standard in almost the same manner as a protein to be measured.

The present invention relates to: a method of quantifying a peptide to be measured by LC/MS/MS by using a peptide having a change in the binding order of amino acids in the amino acid sequence of the peptide to be measured, as an internal standard substance; a method of quantifying a protein to be measured by LC/MS/MS by using a peptide having a change in the binding order of amino acids in the amino acid sequence of the protein to be measured, as an internal standard substance; and a method of quantifying a protein to be measured by LC/MS/MS by using a protein having a change in the binding order of amino acids in the amino acid sequence of the protein to be measured, as an internal standard substance. In the present invention, an amino acid polymer which cannot be cleaved with an enzyme such as trypsin used in measurement is defined as a peptide. Meanwhile, in the present invention, an amino acid polymer which can be cleaved with an enzyme is defined as a protein.

Therefore, the present invention comprises the following constitution.

(1) A method of quantifying a peptide by LC/MS/MS, comprising; peptide having a change in the order of amino acid sequence of the peptide to be measured is used as an internal standard substance.

(2) A method of quantifying a protein by LC/MS/MS, comprising; peptide having a change in the order of amino acid sequence of a protein to be measured is used as an internal standard substance.

(3) A method of quantifying a protein by LC/MS/MS, comprising; protein having a change in the order of amino acid sequence of a protein to be measured is used as an internal standard substance.

(4) A method of quantifying a protein, wherein the protein to be measured is any one of bovine lactoferrin, bovine lactoperoxidase, bovine angiogenin and bovine cystatin C.

A protein or peptide having a change in the binding order of amino acids in the amino acid sequence may be very easily prepared by changing the binding order on a genetic level. The protein or peptide having a change in the binding order of amino acids as an internal standard is thought to behave in almost the same manner as a protein to be measured, and thus a measurement can be achieved with higher accuracy.

In the method of the present invention, the accuracy and specificity can be improved compared to those in single-step MS because selection based on the mass is performed in two steps. Moreover, the method can confirm that only a specific protein is measured because information on the amino acid sequence can be obtained at any time by the second MS. Meanwhile, in a conventional method where a peptide including a deuterium-labeled amino acid is used as an internal standard, the second MS should be performed while switching the measurement of a target peptide and measurement of the internal standard peptide, resulting in lowering the accuracy of the measurement. On the other hand, in the method of the present invention, measurement with high accuracy can be performed because the mass of the target peptide is the same as that of the internal standard peptide. As described above, the method of the present invention can be achieved only by changing the binding order of amino acids in an amino acid sequence, and thus the analysis method is easy. In addition, measurement can be performed without using any expensive and rare reagent. Moreover, the internal standard peptide may be prepared using an existing peptide synthesizer, and thus the method of the present invention has an advantage over the conventional measurement method in terms of cost.

BRIEF DESCRIPTION OF THE DRAWINGS

FIG. 1 illustrates the relationship between the concentration ratio of the peptide to be measured (LFP01) and the internal standard peptide (LFP02) and the area ratio (Example 6) at the time.

DETAILED DESCRIPTION OF THE INVENTION

The present invention relates to: a method of quantifying a peptide to be measured by LC/MS/MS by using a peptide having a change in the binding order of amino acids in the amino acid sequence of the peptide to be measured, as an internal standard substance; a method of quantifying a protein to be measured by LC/MS/MS by using a peptide having a change in the binding order of amino acids in the amino acid sequence of the protein to be measured, as an internal standard substance; and a method of quantifying a protein to be measured by LC/MS/MS by using a protein having a change in the binding order of amino acids in the amino acid sequence of the protein to be measured, as an internal standard substance.

In the methods of the present invention, first, an internal standard peptide having a change in the binding order of amino acids in the amino acid sequence of the peptide to be measured is determined, and the determined peptide is prepared.

In determining the peptide to be used as an internal standard, the peptide which satisfies the following conditions is appropriate.

(1) The peptide is produced by solubilizing a protein with a denaturant which can allow an enzymatic reaction of the protein, decomposing the protein with an endopeptidase, preferably such as trypsin or lysyl endopeptidase, having high specificity for a specific amino acid.

It is because a peptidase having high specificity is desirable because if a protein is decomposed with a peptidase having low specificity in a complex sample system, a change in reaction efficiency may cause a change in the produced amount of the peptide to be measured.

(2) Any peptide in the above item (1) may be used as long as the peptide is ionized by LC/MS. Among peptides obtained by cleaving a protein, a peptide which exhibits high ionization efficiency and high detection sensitivity when detected by LC/MS is preferable.

It is because, if the measurement target is defined to a peptide which is detected at the highest sensitivity, there is a fear in that the peptide may not satisfy the following condition (3), and hence all peptides which can be detected are regarded as the target.

(3) Moreover, in order to use the peptide as an internal standard, any peptide can be used as long as it has a change in part of an amino acid in the amino acid sequence of the peptide described in the item (2) above. Desirably, the peptide eluted at the same retention time in separation by LC/MS is preferable.

It is because, the measurement may be often performed using a substance having different retention time or a completely different substance as internal standards, therefore, the retention time may be not be the same necessarily, but ionization and fragmentation in MS/MS are preferably performed at the same time.

In determining the peptide to be used as an internal standard, the peptide which satisfies the following conditions in addition to the above-described conditions is desirable.

The peptide is not phosphorylated or not modified by sugar chain.
The peptide contains no cysteine.
The peptide is not eluted immediately after the start and just before the end point in chromatography.
The peptide is unlikely to produce polyvalent ions.

Furthermore, measurement is preferably performed while satisfying the following remarks.

(A) Measurement is more preferably performed using a protein to be measured having a partial sequence which is the same as that of the peptide described in the item (3) above, as an internal standard. It is because proteins which have a change in a partial sequence have the same molecular weight and exhibit almost the same behavior in electrophoresis with high separation capability, and the like, because measurement in a complex system may often require an extraction step and the like, but the recover rate of 100% is not actually difficult. Note that it is preferable for the protein to be measured and the protein used as an internal standard are not preferably different in effects of an enzymatic treatment or the like.

(B) Peptides produced by MS/MS are targets for the measurement. The measurement target is preferably a peptide which can be detected at higher sensitivity and has a molecular weight different from that of the peptide to be measured.

After determination of an internal standard peptide having a change in the binding order of amino acids in the amino acid sequence of the peptide to be measured, the internal standard peptide is prepared. The peptide is prepared by a general method such as a solid-phase peptide synthesis or the like. In addition, existing peptide synthesizers such as ABI431A (Boc solid phase method), ABI433A (Fmoc solid phase method) and the like may be used for the peptide preparation. The peptide synthesis method may be a method which is generally performed when the peptide is synthesized using a peptide synthesizer.

By changing the binding order of amino acids in the amino acid sequence of a specific peptide in a protein to be measured, the specific peptide in the protein to be measured and the internal standard peptide behave as substances having the same molecular weight the first MS, and the peptides are separated based on the difference in the amino acid sequences in the second MS. Based on the ratio of the signal intensities depending on each peptide in the second MS, the concentration of the protein to be measured is quantified. In the present invention, quantification by LC/MS/MS is performed as follows. However, the method is a general method when using LC/MS/MS and is not a special method for performing the present invention.

Separation of the peptides is performed by gradient elution using an HPLC system.

Peptides were separated using MAGIC 2002 HPLC system with a column (MAGIC C18 equipped with a 5-μL peptide trap (0.2 mm ID×50 mm)) at a flow rate of 2 μL/min. Gradient elution was performed over 20 minutes using solution A (2% acetonitrile-0.05% formic acid) and solution B (90% acetonitrile-0.05% formic acid) with the range from 2% to 65% of solution B. Ions to be measured were parent ion: m/z 853.8, MS/MS target ion: m/z 876.4 and internal standard target ion: m/z 862.4, and the target range of MS/MS was 860.9 to 877.9. MS was performed using LCQ Advantage.

Hereinafter, the present invention is described in more detail by way of examples and test examples.

However, the descriptions are mere illustration, and the present invention is not limited to these examples.

Note that the amino acids with a underline in internal standard peptides described in examples are the replaced amino acids.

The term "SRM (selected reaction monitoring)" described in the examples refers to measurement of a secondary ion produced by LC/MS/MS as a target and forms a pair with the term "SIM (selected ion monitoring)", which refers to measurement of a primary ion produced by LC/MS as a target.

The term "SRM target" refers to a peptide that is actually measured. A peptide cleaved by enzyme is detected in the first MS, and the peptide is divided at a certain length position having specific lengths by electrical energy in the second MS. The resultant peptides are measured to calculate values. The sequence with a single underline in SRM target represents a part of an amino acid sequence which is measured a produced secondary ion as a target to be measured.

The value "m/z" is calculated by dividing the mass (m) of an ion actually observed in an LC/MS detector by the number of charges (z) thereof. Although the charge state of each peptide is different in an MS apparatus, the actual mass of a peptide (molecular weight M) is calculated by the following mathematical expression:

$$M=((m/z)-1)*z.$$

Note that the term "mono" refers to a monoisotopic mass (molecular weight) obtained by calculating a compositional formula from the isotopic mass of the most abundant naturally occurring isotope.

Example 1

Preparation of Bovine Lactoferrin Internal Standard Peptide

In quantifying a bovine lactoferrin, an internal standard peptide having a change in the binding order of amino acids in the amino acid sequence of the peptide was determined, and then the internal standard peptide was prepared as follows using a peptide synthesizer (Fmoc solid phase method (ABI433A)).

Measuring object peptide (LFP01); MW 1305.645 (mono); m/z 653.83 mono +2

Glu Thr Thr Val PheGluAsnLeuProGluLys (SEQ ID NO: 1)    formula (1)

SRM target; m/z 876.4 mono +1

Glu Thr Thr Val PheGluAsnLeuProGluLys (SEQ ID NO: 1)    formula (1)

Retention time (min); 10.29

Internal standard peptide (LFP02); MW 1305.645(mono), m/z 653.83 mono +2

Glu Thr Thr Leu Phe Glu Asn Val Pro Glu Lys (SEQ ID NO: 2)    formula (2)

SRM target; m/z 876.4 mono +1

Glu Thr Thr LeuPheGluAsnValProGluLys (SEQ ID NO: 2)    formula (2)

Retention time (min); 10.28.

Example 2

Preparation 1 of Bovine Lactoperoxidase Internal Standard Peptide

In quantifying a bovine lactoperoxidase, an internal standard peptide having a change in the binding order of amino acids in the amino acid sequence of the peptide was determined, and then the internal standard peptide was prepared as follows using a peptide synthesizer (Fmoc solid phase method (ABI433A)).

Measuring object peptide 1; MW 1497.765 (mono); m/z 749.89 mono +2

Ser Trp Glu Val Gly Cys Gly Ala Pro Val Pro Leu Val Lys (SEQ ID NO: 3)    formula (3)

SRM target; m/z 652.4 mono +1

Ser Trp Glu Val Gly Cys Gly Ala ProValProLeuValLys (SEQ ID NO: 3)    formula (3)

Retention time (min); 12.10
Internal standard peptide 1

Ser Trp Glu Leu Gly Cys Gly Ala Pro Val Pro Val Val Lys (SEQ ID NO: 4)    formula (4)

SRM target; m/z 638.4 mono +1

Ser Trp Glu Leu Gly Cys Gly Ala ProValProValValLys (SEQ ID NO: 4)    formula (4)

Retention time (min): 12.15.

Example 3

Preparation 2 of Bovine Lactoperoxidase Internal Standard Peptide

In quantifying a bovine lactoperoxidase, an internal standard peptide having a change in the binding order of amino acids in the amino acid sequence of the peptide was determined, and then the internal standard peptide was prepared as follows using a peptide synthesizer (Fmoc solid phase method (ABI433A)).

Measuring object peptide 2; MW 1466.799 (mono); m/z 734.408 mono +2

Ile His Gly Phe Asp Leu Ala Ala Ile Asn Leu Gln Arg (SEQ ID NO: 5)    formula (5)

SRM target; m/z 754.4 mono +1

IleHisGlyPheAspLeuAlaAla Ile Asn Leu Gln Arg (SEQ ID NO: 5)    formula (5)

Retention time (min); 11.42
Internal standard peptide 2; MW 1466.799 (mono), m/z 734.408 mono +2

Ile His Ala Phe Asp Leu Ala Gly Ile Asn Leu Gln Arg (SEQ ID NO: 6)    formula (6)

SRM target; m/z 768.4 mono +1

IleHisAlaPheAspLeuAla Gly Ile Asn Leu Gln Arg (SEQ ID NO: 6)    formula (6)

Retention time (min); 11.36.

Example 4

Preparation of Bovine Angiogenin Internal Standard Peptide

In quantifying a bovine angiogenin, an internal standard peptide having a change in the binding order of amino acids in the amino acid sequence of the peptide was determined, and then the internal standard peptide was prepared as follows using a peptide synthesizer (Fmoc solid phase method (ABI433A)).

Measuring object peptide; MW 1534.757 (mono); m/z 768.386 mono +2

Tyr Ile His Phe Leu Thr Gln His Tyr Asp Ala Lys (SEQ ID NO: 7)    formula (7)

SRM target; m/z 1122.6 mono +1

Tyr Ile His PheLeuThrGlnHisTyrAspAlaLys (SEQ ID NO: 7)    formula (7)

Retention time (min); 9.99
Internal standard peptide; MW 1534.757 (mono), m/z 768.386 mono +2

Tyr Ala His Phe Leu Thr Gln His Tyr Asp Ile Lys (SEQ ID NO: 8)    formula (8)

SRM target; m/z 1164.6 mono +1

Tyr Ala His PheLeuThrGlnHisTyrAspIleLys (SEQ ID NO: 8)    formula (8)

Retention time (min); 9.94.

Example 5

Preparation of Bovine Cystatin C Internal Standard Peptide

In quantifying a bovine cystatin C, an internal standard peptide including an amino acid sequence having a change in the binding order of amino acids in the amino acid sequence of the peptide was determined, and then the internal standard peptide was prepared as follows using a peptide synthesizer (Fmoc solid phase method (ABI433A)).

Measuring object peptide; 1825.903 (mono); m/z 913.96 mono +2

Gln Val Val Ser Gly Met Asn Tyr Phe Leu Asp Val Glu Leu Gly Arg (SEQ ID NO: 9)    formula (9)

SRM target; m/z 948.5 mono +1

Gln Val Val Ser Gly Met Asn Tyr PheLeuAspValGluLeuGlyArg (SEQ ID NO: 9)    formula (9)

Retention time (min) 11.60
Internal standard peptide; MW 1825.903 (mono), m/z 913.96 mono +2

Gln Gly Val Ser Gly Met Asn Tyr Phe Leu Asp Val Glu Leu Val Arg (SEQ ID NO: 10)    formula (10)

SRM target; m/z 990.6 mono +1

Gln Gly Val Ser Gly Met Asn Tyr PheLeuAspValGluLeuValArg (SEQ ID NO: 10)    formula (10)

Retention time (min); 11.58.

Example 6

Quantification of Peptide

A calibration curve was created by varying concentration of the bovine lactoferrin peptide to be measured used in Example 1 (LFP01) in the range between 0.25 and 500 fmol/μL and using the bovine lactoferrin internal standard peptide (LFP02) (10 fmol/μL). The measurement method is as follows. Each of the peptides was dissolved in an aqueous solution of 0.1% formic acid, 0.02% trifluoroacetic acid (TFA), and 2% acetonitrile to reach the predetermined concentration, and 2 μL of each solution was subjected to analysis by LC/MS/MS. The conditions of LC/MS/MS are as follows. Each peptide was separated using MAGIC 2002 HPLC system (Michrom Bioresources, Inc., USA) with a column (MAGIC C18 equipped with a 5-μL peptide trap (0.2 mm ID×50 mm, Michrom Bioresources, Inc., USA)) at a flow rate of 2 μL/min. Gradient elution was performed over 20 minutes with solution A (2% acetonitrile-0.05% formic acid) and solution B (90% acetonitrile-0.05% formic acid) while changing the ratio of solution B from 2% to 65%. Ions to be measured were MS ion: m/z 653.8, MS/MS target ion: m/z 876.4, and internal standard target ion: m/z 862.4, and the target range of MS/MS was 860.9 to 877.9. MS was performed using LCQ Advantage (Thermo Electron Co., USA). The peak area of each peptide was calculated from the resultant chromatogram, and the ratios of areas for the respective peptides were calculated. Table 1 shows the ratios of the areas. Moreover, the concentration ratio of the peptide to be measured (LFP01) and the internal standard peptide (LFP02) and the area ratio at that point are shown in FIG. 1.

In FIG. 1, the horizontal axis represents the molar ratio of the peptide to be measured (LFP01) and the internal standard peptide (LFP02), and the vertical axis represents the ratio of the respective peptides determined by LC/MS/MS. The results reveal that the linearity is maintained in the range of 2,000-fold. In addition, the slope was found to be about 1. From the above results, the peptide to be measured and the internal standard peptide were found to exhibit almost the same behavior in reactions after ionization, that is, the peptide to be measured and the internal standard peptide were found to have almost the same ionization ratio and fragment production rate.

The peak area of each peptide was calculated from the resultant chromatogram, and the ratios of areas for the respective peptides were determined. From the area ratios, the molar ratio of each peptide was determined based on the calibration curve shown in FIG. 1. The concentration of LFP02 when measuring by LC/MS/MS is a value calculated by multiplying 10 fmol/µl by 5/6. The skim milk sample was diluted 10-fold in the enzyme treatment step and diluted 6-fold with the internal standard solution. Therefore, the concentration of the target peptide is calculated by the following expression:

Concentration of the target peptide=molar ratio of each peptide×5/6×10×60.

If the molecular weight of lactoferrin is defined as 80,000, the weight concentration can be determined based on the molar concentration of the target. The lactoferrin content in skim milk could be determined based on the amount of the weighed skim milk. The measurement results are shown in Table 2. The term "CV" is a coefficient of variation calculated by dividing the standard deviation (SD) by the average value and then converting the resultant value into percentage, and represents analytical accuracy.

As shown in Table 2, the CV value is about 8.9%, which is a satisfactory degree of variability.

TABLE 1

| | LFP01 [fmol/uL] | LFP02 [fmol/uL] | Conc. ratio 01/02 | Area LFP01 | Area LFP02 | Area/ratio 01/02 |
|---|---|---|---|---|---|---|
| 1 | 0.244141 | 10 | 0.0244141 | 83598 | 2571729 | 0.032507 |
| 2 | 0.488281 | 10 | 0.0488281 | 107313 | 1654035 | 0.06488 |
| 3 | 0.976563 | 10 | 0.0976563 | 151835 | 1226603 | 0.123785 |
| 4 | 1.953125 | 10 | 0.1953125 | 349436 | 1580818 | 0.221048 |
| 5 | 3.90625 | 10 | 0.390625 | 716557 | 2158181 | 0.332019 |
| 6 | 7.8125 | 10 | 0.78125 | 124167 | 232943 | 0.533036 |
| 7 | 15.625 | 10 | 1.5625 | 1036283 | 920833 | 1.125376 |
| 8 | 31.25 | 10 | 3.125 | 3568835 | 1837996 | 1.941699 |
| 9 | 62.5 | 10 | 6.25 | 19354949 | 3194882 | 6.05811 |
| 10 | 125 | 10 | 12.5 | 45184765 | 3730421 | 12.11251 |
| 11 | 250 | 10 | 25 | 79821523 | 3283706 | 24.30836 |
| 12 | 500 | 10 | 50 | 203636951 | 3739285 | 54.45879 |

Example 7

Measurement of Lactoferrin in Skim Milk

Skim milk was weighed five times a day to prepare samples to be measured. Aqueous solutions containing 13 to 15 mg/ml of skim milk were prepared, and formic acid was added thereto in an amount of 1/1,000 to prepare sample solutions. Each solution (10 µl) was dried up and then dissolved in 20 µl of 0.1 M bicarbonate ammonium containing 8 M urea and 1 mM Tris(carboxyethyl)phosphin (TCEP), and was heated at 56° C. for 30 minutes. The solution was returned to room temperature, and 5 µl of 100 mM iodoacetamide solution was added and reacted for 30 minutes under a light shielding condition. Ultrapure water (54 µl) was added, and 10 µl of 0.1 µg/ml trypsin and 10 µl of 0.1 µg/ml lysyl endopeptidase were added and the mixed solution was reacted at 37° C. for 16 hours. Formic acid (1 µl) was added to stop the reaction, and the resultant solution was used as a peptide solution of sample to be measured. Each sample solution was diluted 6-fold with a solution of 10 fmol/µl internal standard peptide (LFP02) (containing 0.1% formic acid, 0.02% trifluoroacetic acid (TFA), and 2% acetonitrile), and 2.5 µl of the diluted solution was analyzed by LC/MS/MS.

TABLE 2

Lactoferrin content in skim milk

| | [lactoferrin mg/ 100 g- skim milk] Test 1 |
|---|---|
| 1 | 105.87 |
| 2 | 102.20 |
| 3 | 95.37 |
| 4 | 106.92 |
| 5 | 121.23 |
| Average | 106.3 |
| Standard deviation (SD) | 9.5 |
| Analytical precision (CV) % | 8.9 |

Example 8

Measurement of Lactoferrin in Skim Milk

Skim milk was weighed five times to prepare samples to be measured.

A mutant-type bovine lactoferrin including the same sequence as that of the bovine lactoferrin internal standard peptide (LFP02) used in Example 1 was prepared. The mutant-type bovine lactoferrin was used as an internal standard to measure a lactoferrin to be measured in skim milk.

The method was carried out as follows. Aqueous solutions of 15 to 16 mg/ml skim milk were prepared, and formic acid was added thereto in an amount of 1/1,000 to prepare sample solutions. To 10 µl of each sample solution was added with 10 µl of 30 µg/ml mutant-type bovine lactoferrin, and the resultant solution was dried up and then dissolved in 20 µl of 0.1 M bicarbonate ammonium containing 8 M urea and 1 mM Tris (carboxyethyl)phosphin (TCEP). The whole was heated at 56° C. for 30 minutes. The solution was returned to room temperature, and 5 µl of a solution of 100 mM iodoacetamide was added there to and reacted for 30 minutes under a light shielding condition. Ultrapure water (54 µl) was added to the resultant, and 10 µl of 0.1 µg/ml trypsin and 10 µl of 0.1 µg/ml lysyl endopeptidase were added thereto and the mixed solution was reacted at 37° C. for 16 hours. Formic acid (1 µl) was added to stop the reaction, and the resultant solution was used as a peptide solution of the sample to be measured. Each sample solution was diluted 10-fold with an aqueous solution of 0.1% formic acid, 0.02% trifluoroacetic acid (TFA) and 2% acetonitrile, and 2.5 µl of the diluted solution was analyzed by LC/MS/MS.

Each peptide was separated using MAGIC 2002 HPLC system including a column (MAGIC C18 equipped with a 5-µL peptide trap (0.2 mm ID×50 mm)) at a flow rate of 2 µL/min. Gradient elution was performed over 20 minutes with solution A (2% acetonitrile-0.05% formic acid) and solution B (90% acetonitrile-0.05% formic acid) while changing the ratio of solution B from 2% to 65%. Ions to be measured were parent ion: m/z 853.8, MS/MS target ion: m/z 876.4, and internal standard target ion: m/z 862.4, and the target range of MS/MS was 860.9 to 877.9. MS was performed using LCQ Advantage.

The peak area of each peptide was calculated from the resultant chromatogram, and the area ratio of the respective peptides was calculated. The molar ratio of each peptide was calculated from the area ratio based on the calibration curve shown in FIG. 1. The mutant-type bovine lactoferrin and bovine lactoferrin had the same molecular weight, and the concentration of the mutant-type bovine lactoferrin added was 30 µg/ml. Therefore, the concentration of lactoferrin in the skim milk solution was calculated by multiplying the molar ratio of each peptide by 30. The lactoferrin content in skim milk was calculated based on the amount of the weighed skim milk. The measurement results are shown in Table 3.

TABLE 3

| Lactoferrin content in skim milk | |
| --- | --- |
| | [lactoferrin mg/ 100 g- skim milk] Test 1 |
| 1 | 116.65 |
| 2 | 107.74 |
| 3 | 112.26 |
| 4 | 97.76 |
| 5 | 98.24 |
| Average | 106.5 |
| Standard deviation (SD) | 8.4 |
| Analytical precision (CV) % | 7.9 |

As a result, the lactoferrin content in skim milk was 106.5 mg/100 g-skim milk.

The invention claimed is:

1. A method of quantifying a peptide in a sample, comprising:
   i) providing the sample, wherein said peptide is a target peptide having a known amino acid sequence;
   ii) adding to said sample a known quantity of a standard peptide, wherein the standard peptide consists of the same amino acids as the target peptide, but the sequence order of the standard peptide differs from the sequence order of said target peptide;
   iii) analyzing the sample from step ii) by LC/MS/MS;
   iv) calculating a peak area and an area ratio for each of the target peptide and the standard peptide, and then determining a molar ratio for the target peptide based on the known quantity of the standard peptide; and
   v) calculating the concentration of the target peptide from the molar ratio.

2. The method according to claim 1, wherein the peptide in the sample is a peptide from bovine lactoferrin, bovine lactoperoxidase, bovine angiogenin or bovine cystatin C.

3. A method of quantifying a protein in a sample, comprising:
   i) providing the sample, wherein said protein in the sample has been treated with a selected endopeptidase that digests the protein into a target peptide having a known amino acid sequence;
   ii) adding to said sample a known quantity of a standard peptide, wherein the standard peptide consists of the same amino acids as the target peptide, but the sequence order of the standard peptide differs from the sequence order of said target peptide;
   iii) analyzing the sample from step ii) by LC/MS/MS;
   iv) calculating a peak area and an area ratio for each of the target peptide and the standard peptide, and then determining a molar ratio for the target peptide based on the known quantity of the standard peptide; and
   v) calculating the concentration of the target peptide from the molar ratio.

4. The method according to claim 3, wherein the protein is bovine lactoferrin, bovine lactoperoxidase, bovine angiogenin or bovine cystatin C.

5. The method according to claim 3, wherein the sequence of the standard peptide differs from the sequence of the target peptide by at least two amino acids.

6. The method according to claim 3, wherein the protein is bovine lactoferrin,
   the target peptide is Glu-Thr-Thr-Val-Phe-Glu-Asn-Leu-Pro-Glu-Lys (SEQ ID NO: 1), and
   the standard peptide is Glu-Thr-Thr-Leu-Phe-Glu-Asn-Val-Pro-Glu-Lys (SEQ ID NO: 2).

7. The method according to claim 3, wherein the protein is bovine lactoperoxidase,
   the target peptide is Ser-Trp-Glu-Val-Gly-Cys-Gly-Ala-Pro-Val-Pro-Leu-Val-Lys (SEQ ID NO: 3), and
   the standard peptide is Ser-Trp-Glu-Leu-Gly-Cys-Gly-Ala-Pro-Val-Pro-Val-Val-Lys (SEQ ID NO: 4).

8. The method according to claim 3, wherein the protein is bovine lactoperoxidase,
   the target peptide is Ile-His-Gly-Phe-Asp-Leu-Ala-Als-Ile-Asn-Leu-Gln-Arg (SEQ ID NO: 5), and
   the standard peptide is lactoperoxidase and the standard peptide is Ile-His-Ala-Phe-Asp-Leu-Ala-Gly-Ile-Asn-Leu-Gln-Arg (SEQ ID NO: 6).

9. The method according to claim 3, wherein the protein is bovine angiogenin,
   the target peptide is Tyr-Ile-His-Phe-Leu-Thr-Gln-His-Tyr-Asp-Ala-Lys (SEQ ID NO: 7), and
   the standard peptide is Tyr-Ala-His-Phe-Leu-Thr-Gln-His-Tyr-Asp-Ile-Lys (SEQ ID NO: 8).

10. The method according to claim 3, wherein the protein is bovine cystatin C,
    the target peptide is Gln-Val-Val-Ser-Gly-Met-Asn-Tyr-Phe-Leu-Asp-Val-Glu-Leu-Gly-Arg (SEQ ID NO: 9), and
    the standard peptide is Gln-Gly-Val-Ser-Gly-Met-Asn-Tyr-Phe-Leu-Asp-Val-Glu-Leu-Val-Arg (SEQ ID NO: 10).

11. The method according to claim 3, wherein the endopeptidase comprises trypsin, lysyl endopeptidase or a mixture thereof.

12. A method of quantifying a protein in a sample, comprising:
    i) providing the sample, wherein said protein is a target protein having a known amino acid sequence;
    ii) adding to said sample a known quantity of a standard protein, wherein the standard protein consists of the same amino acids as the target protein, but the sequence order of the standard protein differs from the sequence order of said target protein;
    iii) analyzing the sample from step ii) by LC/MS/MS;
    iv) calculating a peak area and an area ratio for each of the target protein and the standard protein, and then determining a molar ratio for the target protein based on the known quantity of the standard protein; and
    v) calculating the concentration of the target protein from the molar ratio.

13. The method according to claim 12, wherein the protein is bovine lactoferrin, bovine lactoperoxidase, bovine angiogenin or bovine cystatin C.

* * * * *

SEQUENCE LISTING

```
<160> NUMBER OF SEQ ID NOS: 10

<210> SEQ ID NO 1
<211> LENGTH: 11
<212> TYPE: PRT
<213> ORGANISM: bovine

<400> SEQUENCE: 1

Glu Thr Thr Val Phe Glu Asn Leu Pro Glu Lys
1               5                   10

<210> SEQ ID NO 2
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 2

Glu Thr Thr Leu Phe Glu Asn Val Pro Glu Lys
1               5                   10

<210> SEQ ID NO 3
<211> LENGTH: 14
<212> TYPE: PRT
<213> ORGANISM: bovine

<400> SEQUENCE: 3

Ser Trp Glu Val Gly Cys Gly Ala Pro Val Pro Leu Val Lys
1               5                   10
```

```
<210> SEQ ID NO 4
<211> LENGTH: 14
<212> TYPE: PRT
<213> ORGANISM: Artificial Sequence
<220> FEATURE:
<223> OTHER INFORMATION: Synthetic Peptide

<400> SEQUENCE: 4

Ser Trp Glu Leu Gly Cys Gly Ala Pro Val Pro Val Val Lys
1               5                   10

<210> SEQ ID NO 5
<211> LENGTH: 13
<212> TYPE: PRT
<213> ORGANISM: bovine

<400> SEQUENCE: 5

Ile His Gly Phe Asp Leu Ala Ala Ile Asn Leu Gln Arg
1               5                   10

<210> SEQ ID NO 6
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 6

Ile His Ala Phe Asp Leu Ala Gly Ile Asn Leu Gln Arg
1               5                   10

<210> SEQ ID NO 7
<211> LENGTH: 12
<212> TYPE: PRT
<213> ORGANISM: bovine

<400> SEQUENCE: 7

Tyr Ile His Phe Leu Thr Gln His Tyr Asp Ala Lys
1               5                   10

<210> SEQ ID NO 8
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 8

Tyr Ala His Phe Leu Thr Gln His Tyr Asp Ile Lys
1               5                   10

<210> SEQ ID NO 9
<211> LENGTH: 16
<212> TYPE: PRT
<213> ORGANISM: bovine

<400> SEQUENCE: 9

Gln Val Val Ser Gly Met Asn Tyr Phe Leu Asp Val Glu Leu Gly Arg
1               5                   10                  15

<210> SEQ ID NO 10
<211> LENGTH: 16
<212> TYPE: PRT
<213> ORGANISM: Artificial Sequence
<220> FEATURE:
<223> OTHER INFORMATION: Synthetic Peptide
```

```
<400> SEQUENCE: 10

Gln Gly Val Ser Gly Met Asn Tyr Phe Leu Asp Val Glu Leu Val Arg
1               5                   10                  15
```